(12) United States Patent
Hauck et al.

(10) Patent No.: US 8,551,084 B2
(45) Date of Patent: *Oct. 8, 2013

(54) RADIO FREQUENCY ABLATION SERVO CATHETER AND METHOD

(75) Inventors: John A. Hauck, Shoreview, MN (US); Eric Olson, Maplewood, MN (US); Jeff A. Schweitzer, St. Paul, MN (US); Jeff Burell, Coon Rapids, MN (US); Mark T. Johnson, Mounds View, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 86 days.

This patent is subject to a terminal disclaimer.

(21) Appl. No.: 13/532,266

(22) Filed: Jun. 25, 2012

(65) Prior Publication Data
US 2012/0303013 A1 Nov. 29, 2012

Related U.S. Application Data

(63) Continuation of application No. 12/638,814, filed on Dec. 15, 2009, now Pat. No. 8,206,383, which is a continuation of application No. 11/139,908, filed on May 27, 2005, now Pat. No. 7,632,265.

(60) Provisional application No. 60/575,741, filed on May 28, 2004.

(51) Int. Cl.
*A61B 18/18* (2006.01)

(52) U.S. Cl.
USPC .............................. 606/34; 606/32; 606/41

(58) Field of Classification Search
USPC .................... 606/32–41; 604/95.04, 95.05
See application file for complete search history.

(56) References Cited

U.S. PATENT DOCUMENTS

| 4,510,574 | A | 4/1985 | Guittet et al. |
| 4,710,876 | A | 12/1987 | Cline et al. |
| 4,837,734 | A | 6/1989 | Ichikawa et al. |
| 4,854,324 | A | 8/1989 | Hirschman et al. |

(Continued)

FOREIGN PATENT DOCUMENTS

| EP | 1779802 | 5/2007 |
| WO | WO-97/44089 | 11/1997 |

(Continued)

OTHER PUBLICATIONS

Supplementary European Search Report, EP08798257, dated Aug. 17, 2011.

(Continued)

*Primary Examiner* — Linda Dvorak
*Assistant Examiner* — Amanda Scott
(74) *Attorney, Agent, or Firm* — Wiley Rein LLP

(57) ABSTRACT

A system that interfaces with a workstation endocardial mapping system allows for the rapid and successful ablation of cardiac tissue. The system allows a physician to see a representation of the physical location of a catheter in a representation of an anatomic model of the patient's heart. The workstation is the primary interface with the physician. A servo catheter having pull wires and pull rings for guidance and a servo catheter control system are interfaced with the workstation. Servo catheter control software may run on the workstation. The servo catheter is coupled to an RF generator. The physician locates a site for ablation therapy and confirms the location of the catheter. Once the catheter is located at the desired ablation site, the physician activates the RF generator to deliver the therapy.

20 Claims, 5 Drawing Sheets

(56) References Cited

U.S. PATENT DOCUMENTS

| | | |
|---|---|---|
| 4,873,572 A | 10/1989 | Miyazaki et al. |
| 4,921,482 A | 5/1990 | Hammerslag et al. |
| 5,078,140 A | 1/1992 | Kwoh |
| 5,114,414 A | 5/1992 | Buchbinder |
| 5,199,950 A | 4/1993 | Schmitt et al. |
| 5,222,501 A | 6/1993 | Ideker et al. |
| RE34,502 E | 1/1994 | Webster |
| 5,281,220 A | 1/1994 | Blake |
| 5,339,799 A | 8/1994 | Kami et al. |
| 5,368,564 A | 11/1994 | Savage |
| 5,385,148 A | 1/1995 | Lesh et al. |
| 5,389,073 A | 2/1995 | Imran |
| 5,391,147 A | 2/1995 | Imran et al. |
| 5,391,199 A | 2/1995 | Ben-Haim |
| 5,396,887 A | 3/1995 | Imran |
| 5,400,783 A | 3/1995 | Pomeranz et al. |
| 5,404,638 A | 4/1995 | Imran |
| 5,406,946 A | 4/1995 | Imran |
| 5,409,000 A | 4/1995 | Imran |
| 5,415,166 A | 5/1995 | Imran |
| 5,423,811 A | 6/1995 | Imran et al. |
| 5,425,364 A | 6/1995 | Imran |
| 5,425,375 A | 6/1995 | Chin et al. |
| 5,431,645 A | 7/1995 | Smith et al. |
| 5,465,717 A | 11/1995 | Imram et al. |
| 5,476,100 A | 12/1995 | Galel |
| 5,478,330 A | 12/1995 | Imran et al. |
| 5,492,131 A | 2/1996 | Galel |
| 5,496,311 A | 3/1996 | Abele et al. |
| 5,498,239 A | 3/1996 | Galel et al. |
| 5,507,802 A | 4/1996 | Imran |
| 5,527,279 A | 6/1996 | Imran |
| 5,533,967 A | 7/1996 | Imran |
| 5,545,161 A | 8/1996 | Imran |
| 5,558,073 A | 9/1996 | Pomeranz et al. |
| 5,578,007 A | 11/1996 | Imran |
| 5,588,964 A | 12/1996 | Imran et al. |
| 5,607,462 A | 3/1997 | Imran |
| 5,632,734 A | 5/1997 | Galel et al. |
| 5,656,029 A | 8/1997 | Imran et al. |
| 5,658,278 A | 8/1997 | Imran et al. |
| 5,673,704 A | 10/1997 | Marchlinski et al. |
| 5,680,860 A | 10/1997 | Imran |
| 5,681,280 A | 10/1997 | Rusk et al. |
| 5,697,927 A | 12/1997 | Imran et al. |
| 5,722,401 A | 3/1998 | Pietroski et al. |
| 5,730,128 A | 3/1998 | Pomeranz et al. |
| 5,754,741 A | 5/1998 | Wang et al. |
| 5,782,899 A | 7/1998 | Imran |
| RE35,880 E | 8/1998 | Waldman et al. |
| 5,800,482 A | 9/1998 | Pomeranz et al. |
| 5,808,665 A | 9/1998 | Green |
| 5,813,991 A | 9/1998 | Willis et al. |
| 5,820,568 A | 10/1998 | Willis |
| 5,823,199 A | 10/1998 | Hastings et al. |
| 5,835,458 A | 11/1998 | Bischel et al. |
| 5,861,024 A | 1/1999 | Rashidi |
| 5,876,325 A | 3/1999 | Mizuno et al. |
| 5,882,333 A | 3/1999 | Schaer et al. |
| 5,882,346 A | 3/1999 | Pomeranz et al. |
| 5,895,417 A | 4/1999 | Pomeranz et al. |
| 5,906,605 A | 5/1999 | Coxum |
| 5,908,446 A | 6/1999 | Imran |
| 5,940,240 A | 8/1999 | Kupferman |
| 5,964,732 A | 10/1999 | Willard |
| 5,964,796 A | 10/1999 | Imran |
| 5,971,967 A | 10/1999 | Willard |
| 5,993,462 A | 11/1999 | Pomeranz et al. |
| 5,997,532 A | 12/1999 | McLaughlin et al. |
| 6,004,271 A | 12/1999 | Moore |
| 6,010,500 A | 1/2000 | Sherman et al. |
| 6,014,579 A | 1/2000 | Pomeranz et al. |
| 6,015,407 A | 1/2000 | Rieb et al. |
| 6,032,077 A | 2/2000 | Pomeranz |
| 6,049,732 A | 4/2000 | Panescu et al. |
| 6,063,022 A | 5/2000 | Ben-Haim |
| 6,066,125 A | 5/2000 | Webster, Jr. |
| 6,083,170 A | 7/2000 | Ben-Haim |
| 6,089,235 A | 7/2000 | Hastings et al. |
| 6,096,004 A | 8/2000 | Meglan et al. |
| 6,119,041 A | 9/2000 | Pomeranz et al. |
| 6,123,699 A | 9/2000 | Webster, Jr. |
| 6,197,017 B1 | 3/2001 | Brock et al. |
| 6,210,362 B1 | 4/2001 | Ponzi |
| 6,216,027 B1 | 4/2001 | Willis et al. |
| 6,221,060 B1 | 4/2001 | Willard |
| 6,227,077 B1 | 5/2001 | Chiang |
| 6,235,022 B1 | 5/2001 | Hallock et al. |
| 6,236,883 B1 | 5/2001 | Ciaccio et al. |
| 6,241,666 B1 | 6/2001 | Pomeranz et al. |
| 6,258,060 B1 | 7/2001 | Willard |
| 6,272,371 B1 | 8/2001 | Shlomo |
| 6,285,898 B1 | 9/2001 | Ben-Haim |
| 6,289,239 B1 | 9/2001 | Panescu et al. |
| 6,292,681 B1 | 9/2001 | Moore |
| 6,298,257 B1 | 10/2001 | Hall et al. |
| 6,375,471 B1 | 4/2002 | Wendlandt et al. |
| 6,398,755 B1 | 6/2002 | Belef et al. |
| 6,432,112 B2 | 8/2002 | Brock et al. |
| 6,436,107 B1 | 8/2002 | Wang et al. |
| 6,451,027 B1 | 9/2002 | Cooper et al. |
| 6,490,474 B1 | 12/2002 | Willis et al. |
| 6,493,608 B1 | 12/2002 | Niemeyer |
| 6,500,167 B1 | 12/2002 | Webster |
| 6,516,211 B1 | 2/2003 | Acker et al. |
| 6,517,477 B1 | 2/2003 | Wendlandt |
| 6,554,820 B1 | 4/2003 | Chin et al. |
| 6,554,844 B2 | 4/2003 | Lee et al. |
| 6,569,160 B1 | 5/2003 | Goldin et al. |
| 6,572,554 B2 | 6/2003 | Yock |
| 6,596,084 B1 | 7/2003 | Patke |
| 6,620,202 B2 | 9/2003 | Bottcher et al. |
| 6,650,920 B2 | 11/2003 | Schaldach et al. |
| 6,659,956 B2 | 12/2003 | Barzell et al. |
| 6,663,622 B1 | 12/2003 | Foley et al. |
| 6,679,269 B2 | 1/2004 | Swanson |
| 6,679,836 B2 | 1/2004 | Couvillon |
| 6,692,485 B1 | 2/2004 | Brock et al. |
| 6,695,785 B2 | 2/2004 | Brisken et al. |
| 6,699,179 B2 | 3/2004 | Wendlant |
| 6,716,190 B1 | 4/2004 | Glines et al. |
| 6,718,196 B1 | 4/2004 | Mah et al. |
| 6,719,804 B2 | 4/2004 | St. Pierre |
| 6,726,675 B1 | 4/2004 | Beyar |
| 6,728,562 B1 | 4/2004 | Budd et al. |
| 6,731,976 B2 | 5/2004 | Penn et al. |
| 6,752,800 B1 | 6/2004 | Winston et al. |
| 6,764,450 B2 | 7/2004 | Yock |
| 6,770,027 B2 | 8/2004 | Bunik et al. |
| 6,783,521 B2 | 8/2004 | Ponzi et al. |
| 6,810,281 B2 | 10/2004 | Brock et al. |
| 6,817,974 B2 | 11/2004 | Cooper et al. |
| 6,835,173 B2 | 12/2004 | Couvillon et al. |
| 6,837,867 B2 | 1/2005 | Kortelling |
| 6,843,793 B2 | 1/2005 | Brock et al. |
| 6,858,003 B2 | 2/2005 | Evans et al. |
| 6,860,878 B2 | 3/2005 | Brock |
| 6,872,178 B2 | 3/2005 | Weinberg |
| 6,874,789 B2 | 4/2005 | Shedlov |
| 6,892,091 B1 | 5/2005 | Ben-Haim et al. |
| 6,913,594 B2 | 7/2005 | Coleman et al. |
| 6,926,669 B1 | 8/2005 | Stewart et al. |
| 6,946,092 B1 | 9/2005 | Bertolino et al. |
| 6,949,106 B2 | 9/2005 | Brock et al. |
| 6,955,674 B2 | 10/2005 | Eick et al. |
| 6,962,669 B2 | 11/2005 | Foreman et al. |
| 6,974,455 B2 | 12/2005 | Garabedian et al. |
| 6,974,465 B2 | 12/2005 | Belef et al. |
| 6,997,870 B2 | 2/2006 | Couvillon |
| 7,022,077 B2 | 4/2006 | Mourad et al. |
| 7,025,064 B2 | 4/2006 | Wang et al. |
| 7,027,892 B2 | 4/2006 | Wang et al. |
| 7,037,345 B2 | 5/2006 | Bottcher et al. |
| 7,189,208 B1 | 3/2007 | Beatty et al. |

| | | |
|---|---|---|
| 7,344,533 B2 | 3/2008 | Pearson et al. |
| 7,479,106 B2 | 1/2009 | Banik et al. |
| 7,632,265 B2 | 12/2009 | Hauck et al. |
| 7,806,829 B2 | 10/2010 | Hauck |
| 2001/0027316 A1 | 10/2001 | Gregory |
| 2002/0042570 A1 | 4/2002 | Schaldach et al. |
| 2002/0045809 A1 | 4/2002 | Ben-Haim |
| 2002/0087166 A1 | 7/2002 | Brock et al. |
| 2002/0087169 A1 | 7/2002 | Brock et al. |
| 2002/0123749 A1 | 9/2002 | Jain |
| 2002/0128633 A1 | 9/2002 | Brock et al. |
| 2002/0143319 A1 | 10/2002 | Brock |
| 2002/0143326 A1 | 10/2002 | Foley et al. |
| 2002/0177789 A1 | 11/2002 | Ferry et al. |
| 2003/0036696 A1 | 2/2003 | Willis et al. |
| 2003/0055410 A1 | 3/2003 | Evans et al. |
| 2004/0049205 A1 | 3/2004 | Lee et al. |
| 2004/0059237 A1 | 3/2004 | Narayan et al. |
| 2004/0073206 A1 | 4/2004 | Foley et al. |
| 2004/0098075 A1 | 5/2004 | Lee |
| 2004/0128026 A1 | 7/2004 | Harris |
| 2004/0176751 A1 | 9/2004 | Weitzner et al. |
| 2004/0193146 A1 | 9/2004 | Lee et al. |
| 2005/0004579 A1 | 1/2005 | Sneider et al. |
| 2005/0049580 A1 | 3/2005 | Brock et al. |
| 2005/0096643 A1 | 5/2005 | Brucker et al. |
| 2005/0102017 A1 | 5/2005 | Mattison |
| 2005/0137478 A1 | 6/2005 | Younge et al. |
| 2005/0192488 A1 | 9/2005 | Bryenton et al. |
| 2005/0197530 A1 | 9/2005 | Wallace et al. |
| 2005/0203382 A1 | 9/2005 | Govari et al. |
| 2005/0203394 A1 | 9/2005 | Hauck |
| 2005/0215983 A1 | 9/2005 | Brock |
| 2005/0216033 A1 | 9/2005 | Lee |
| 2005/0222554 A1 | 10/2005 | Wallace et al. |
| 2005/0228440 A1 | 10/2005 | Brock et al. |
| 2005/0234437 A1 | 10/2005 | Baxter et al. |
| 2006/0004352 A1 | 1/2006 | Vaska et al. |
| 2006/0052695 A1 | 3/2006 | Adam |
| 2006/0057560 A1 | 3/2006 | Hlavka et al. |
| 2006/0058692 A1 | 3/2006 | Beatty et al. |
| 2006/0084945 A1 | 4/2006 | Moll et al. |
| 2006/0084960 A1 | 4/2006 | Mester et al. |
| 2006/0095022 A1 | 5/2006 | Moll et al. |
| 2006/0098010 A1 | 5/2006 | Dwyer et al. |
| 2006/0100610 A1 | 5/2006 | Wallace et al. |
| 2006/0111692 A1 | 5/2006 | Moll et al. |
| 2006/0116575 A1 | 6/2006 | Willis |
| 2006/0149139 A1 | 7/2006 | Bonmassar et al. |
| 2006/0258935 A1 | 11/2006 | Pile-Spellman et al. |
| 2007/0021679 A1 | 1/2007 | Narayan et al. |
| 2007/0185485 A1 | 8/2007 | Hauck et al. |
| 2007/0197896 A1 | 8/2007 | Moll et al. |

FOREIGN PATENT DOCUMENTS

| | | |
|---|---|---|
| WO | WO-00/07501 | 2/2000 |
| WO | WO-00/07503 | 2/2000 |
| WO | WO-01/25822 | 4/2001 |
| WO | WO-2004/047632 | 6/2004 |
| WO | WO-2005/042053 | 5/2005 |
| WO | WO-2005/044081 | 5/2005 |
| WO | WO-2005/112750 | 12/2005 |
| WO | WO-2005/117596 | 12/2005 |
| WO | WO-2006/059089 | 6/2006 |
| WO | WO-2007/005976 | 1/2007 |

OTHER PUBLICATIONS

International Search Report and Written Opinion, PCT/US2007/080698, May 13, 2008.

International Search Report and Written Opinion, PCT/US2007/080701, Apr. 15, 2008.

International Search Report and Written Opinion, PCT/US2007/080702, Oct. 8, 2007.

International Search Report and Written Opinion, PCT/US2007/080703, Oct. 8, 2007.

International Search Report and Written Opinion, PCT/US2007/080705, Oct. 8, 2007.

International Search Report and Written Opinion, PCT/US2008/073694 Nov. 13, 2008.

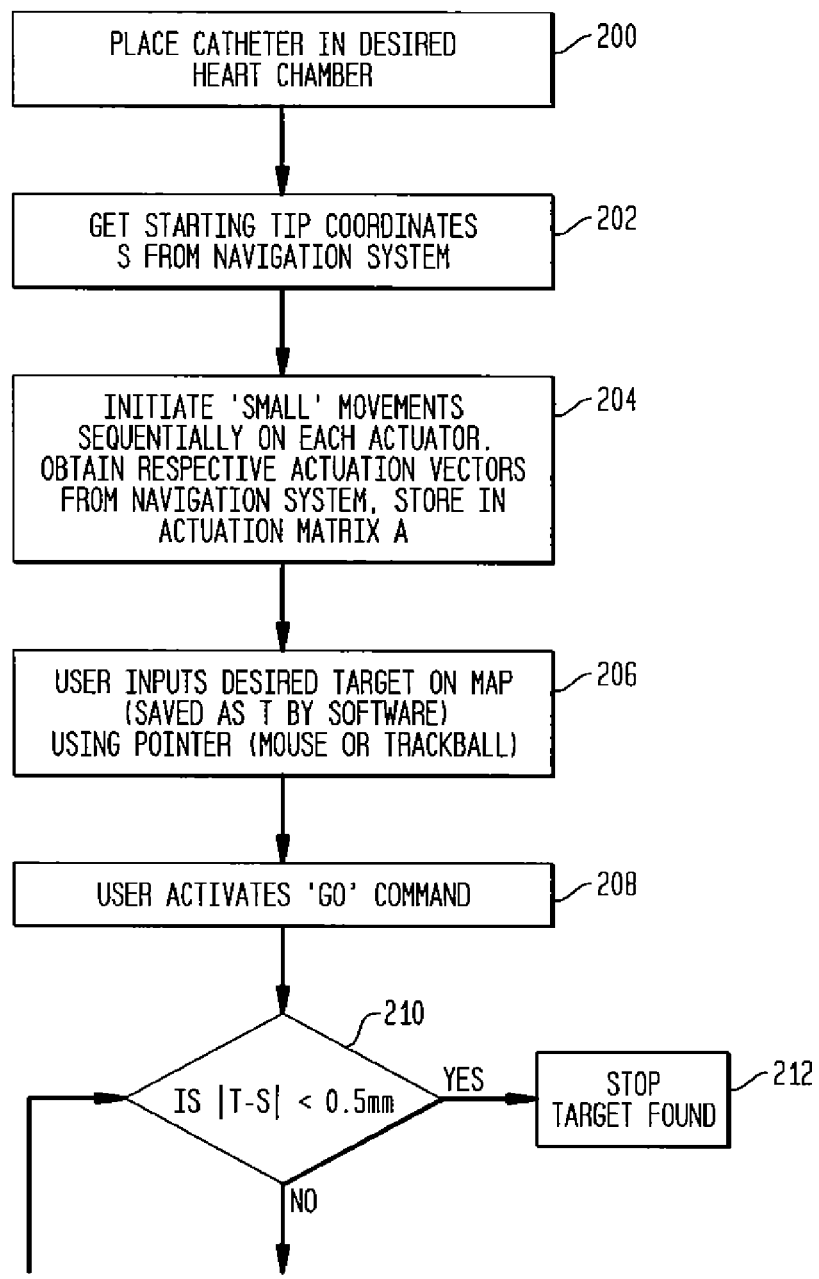

RADIO FREQUENCY ABLATION SERVO CATHETER AND METHOD

CROSS-REFERENCE TO RELATED APPLICATIONS

This application is a continuation of U.S. application Ser. No. 12/638,814 ("the '814 application"), filed 15 Dec. 2009 now U.S. Pat. No. 8,206,383, which is a continuation of U.S. application Ser. No. 11/139,908 ("the '908 application"), filed 27 May 2005, now U.S. Pat. No. 7,632,265 ("the '265 patent"), issued 15 Dec. 2009, which claims priority to U.S. provisional application No. 60/575,741 ("the '741 application"), filed 28 May 2004. The '814, '908, and '741 applications and the '265 patent are hereby incorporated by reference in their entirety as though fully set forth herein.

BACKGROUND OF THE INVENTION a. Field of the Invention

The present invention relates generally to radio frequency ablation catheter systems and more particularly to an interactive and automated catheter for producing lesions to treat arrhythmias in the atrium of a patient's heart.

b. Background Art

Many atrial arrhythmias are caused by anatomical accessory pathways in the heart, which provide spurious conduction paths. Conduction of electrical depolarization's along these pathways within a chamber gives rise to arrhythmias. Although drugs have been used to treat such arrhythmias for many years, cardiac ablation, or destruction of localized regions of tissue, can provide a permanent cure for the patient. For this reason cardiac ablation is preferred in many instances. This treatment is especially preferred for patients that experience detrimental effects from drugs.

Cardiac ablation has traditionally been a tedious procedure performed under fluoroscopy by a physician who sequentially maps the electrical potentials within the heart using a manually directed EP catheter. Once an appropriate site has been selected identified and selected for ablation, RF energy is delivered to the site. Ablation energy is typically delivered through the same catheter used to "map". The purpose of the ablation is to destroy a small bolus of tissue at the location. This tissue lesion can no longer conduct and the arrhythmia is interrupted and the arrhythmia stops.

One common intervention is ablation around the annulus or the ostium of the pulmonary vein that is located in the left atrium. However, navigating to this location reliably and sequentially and delivering electrical energy is an extremely tedious procedure requiring substantial amount of skill and time to complete successfully.

For this reason there is a continuing need to improve catheter technology.

BRIEF SUMMARY OF THE INVENTION

The present invention provides a system that allows for the automated rapid and successful ablation of cardiac tissue. The overall system interfaces with an Endocardial Solutions Ensite "work station" endocardial mapping system of the type sold by Endocardial Solutions, Inc. of St. Paul, Minn., or other equivalent devices.

The "Ensite" system is preferred as it includes a "NavX" feature that allows the physician to see a representation of the physical location of his catheter in a presentation of an anatomic model of the patient's heart.

The system includes a "servo catheter" and a servo catheter control system that are interfaced with the work station. The work station is the primary interface with the physician and it is anticipated that the servo catheter control software will run on the work station. The servo catheter will also be coupled to a conventional RF generator.

In use the physician will locate site for ablation therapy and then he will confirm the location of the catheter which will automatically navigate to the lesion site desired by the physician. Once the catheter is located at that desired point or site the physician will activate the RF generator to deliver the therapy.

BRIEF DESCRIPTION OF THE DRAWINGS

Throughout the several drawings identical reference numerals indicate identical structure wherein:

FIG. 4A is a flow chart representation of a method of the system;

DETAILED DESCRIPTION OF THE INVENTION

Overview

For purposes of this disclosure the NavX features of the Ensite system as sold by ESI of St Paul Minn., allows for the creation of a chamber geometry reflecting the chamber of interest within the heart. In a preferred embodiment a mapping catheter is swept around the chamber by the physician to create a geometry for the chamber. Next the physician will identify fiducial points in the physical heart that are used to create a base map of the heart model. This base map may be merged with a CT or MRI image to provide an extremely high resolution, highly detailed anatomic map image of the chamber of the heart. Or in the alternative the base map may be used for the method. The physician identifies regions of this model heart for ablation by interacting with a computer terminal and for example using a mouse to lay down a collection of target points which he intends to ablate with RF energy.

In summary the servo catheter is also interfaced with the Ensite system and makes use of the NavX catheter navigation and visualization features of NavX. In operation the physician navigates the servo catheter to the approximate location of the therapy and a relatively complicated control system is invoked that navigates the servo catheter tip to various locations sequentially identified by the physician. Once in place and after its position is verified the physician will activate the RF generator to provide the ablation therapy.

Servo Catheter

Figure 5:
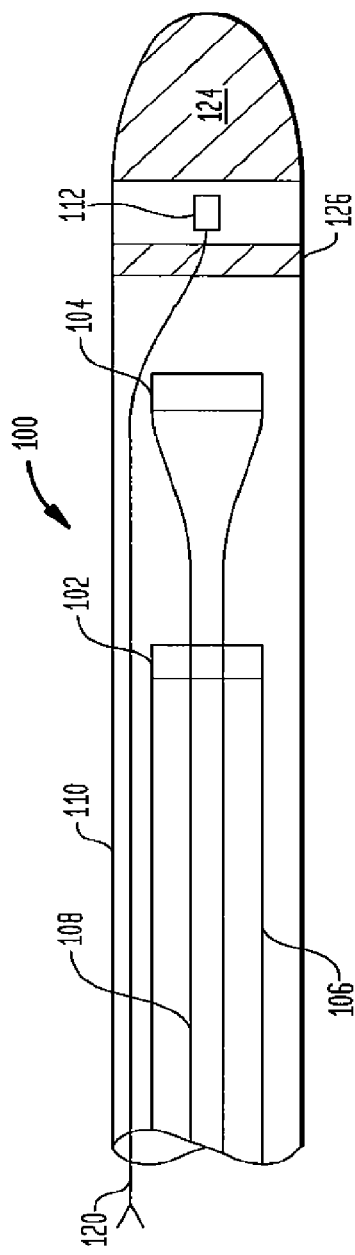
FIG. 5 is a representation of a servo catheter of the system.
Figure 6:
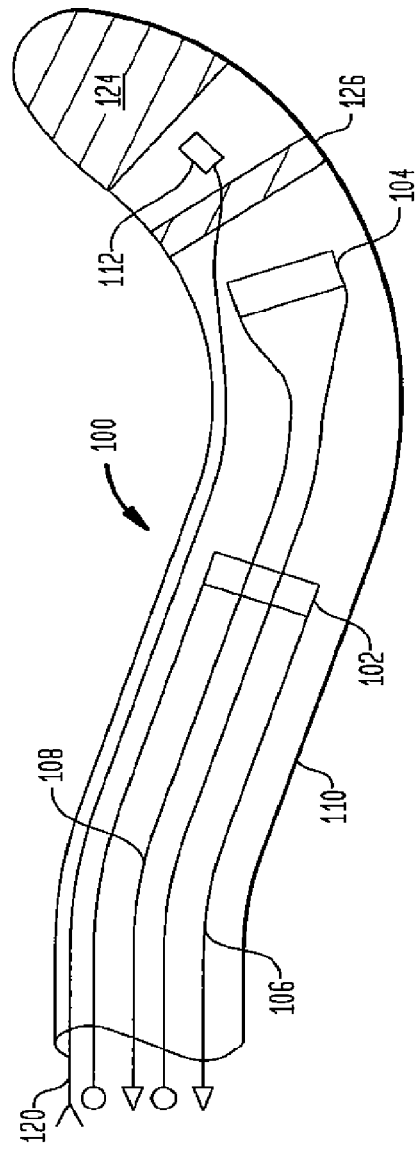
FIG. 6 is a representation of a servo catheter of the system.

The catheter has a number of attributes that permit the device to carry out this function. An illustrative and not limiting prototype version of the device is seen in FIG. 5 and FIG. 6. The catheter 100 has been constructed with eight pull wires (of which 4 are shown for clarity) and two associated pull rings labeled 102 and 104 in the figures.

Figure 1:
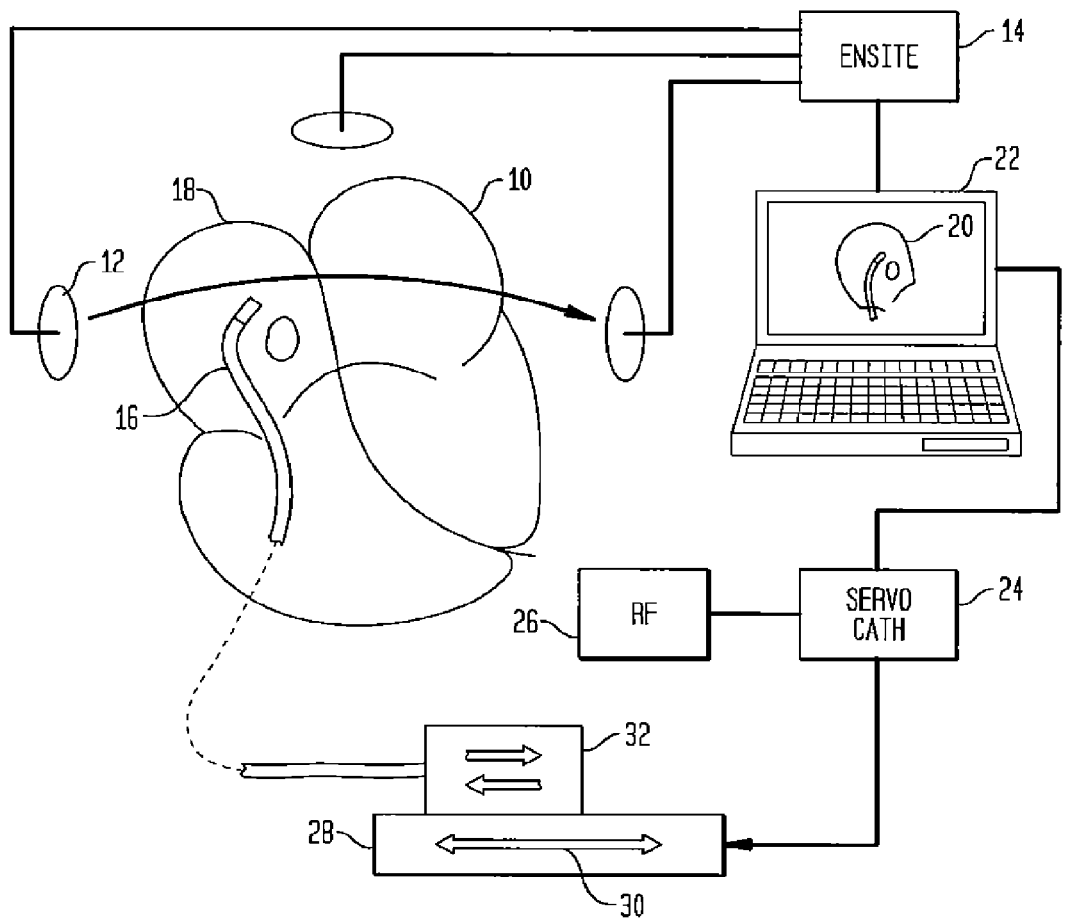
FIG. 1 is a schematic representation of the overall system.

The pull wires typified by pull wire 106 and 108 are manipulated by servo mechanisms, such as stepper or driven ball screw slides illustrated in FIG. 1. These mechanisms displace the wire with respect to the catheter body 110 and under tension pull and shape the catheter in a particular direction. The use of multiple wires and multiple pull rings allows for very complex control over the catheter's position, shape and stiffness, all of which are important to carry out the ultimate therapy desired by the physician. Multiple pull rings and multiple individual wires permits control over the stiffness of the catheter which is used to conform the shape of the catheter so that the entire carriage may be advanced on a ball screw to move the catheter against the wall of the heart.

At least one force transducer 112 is located within the catheter provide feedback to the control system to prevent perforation of the heart and to otherwise enhance the safety of the unit. Preferably the force transducer takes the form of a strain gauge 112 coupled to the control system via connection 120.

The catheter distal tip will carry an ablation electrode 124 coupled via a connection not shown to the RF generator as is known in the art. It is preferred to have a separate location electrode 126 for use by the Ensite system as is known in the art. Once again no connection is shown to simply the figure for clarity.

As seen in FIG. 6 pulling on pull wire 108 deflects the distal tip while pulling on pull wire 106 deflects the body 110 of the catheter. Since each wire is independent of the others the computer system may control both the stiffness and deflection of the catheter in a way not achieved by physician control of the wires. In general the physician will use a joystick of other input device to control the catheter. However, this control system also invokes many of the automated procedures of the servo catheter and is not strictly a direct manipulator.

Although robotic control has made great headway in surgery most conventional systems use a stereotactic frame to position the device and the coordinate systems with respect to the patient. One challenge of the current system is the fact that the target tissue is moving because the heart is beating and the catheter within the heart is displaced and moved by heart motion as well so that there is no permanently fixed relationship between the catheter and its coordinate system, the patient and its coordinate system, and the patient and its coordinate system at the target site. This issue is complicated by and exacerbated by the fact that the map may not be wholly accurate as well, so the end point or target point's location in space is not well resolved.

Operation Overview

Turning to FIG. 1 there is shown a patient's heart 10 in isolation. A series of patch electrodes are applied to the surface of the patient (not shown) typified by patch 12. These are coupled to an Ensite catheter navigation system 14 which locates the tip of the Servo catheter 16 in the chamber 18 of the patient's heart. The Ensite system is capable of using this catheter or another catheter to create a map of the chamber of the heart shown as image 20 on monitor 22 of a computer system. In operation the physician interacts with the model image 20 and maps out and plans an RF ablation intervention that is applied to the Servo catheter 16 through its proximal connection to the Servo catheter interface box 24. The interface box allows RF energy from generator 26 to enter the catheter upon the command of the physician and ablate tissue in the cardiac chamber. Critical to the operation of the servo catheter is the translation mechanism 28, which provides a carriage for translating the catheter proximal end advancing or retracting the catheter from the chamber as indicated by motion arrow 30. An additional group of sensors and actuators or other servo translation mechanism 32 are coupled to the proximal end of the catheter 16 to allow the device to be steered automatically by software running on the Ensite 14 workstation.

Thus, in brief overview, the physician navigates the catheter into the chamber of interest, identifies locations of interest within that chamber which he desires to ablate, then the Servo mechanism moves the catheter to various locations requested by the physician and once in position the physician administers RF radiation to provide a therapeutic intervention.

Figure 2:
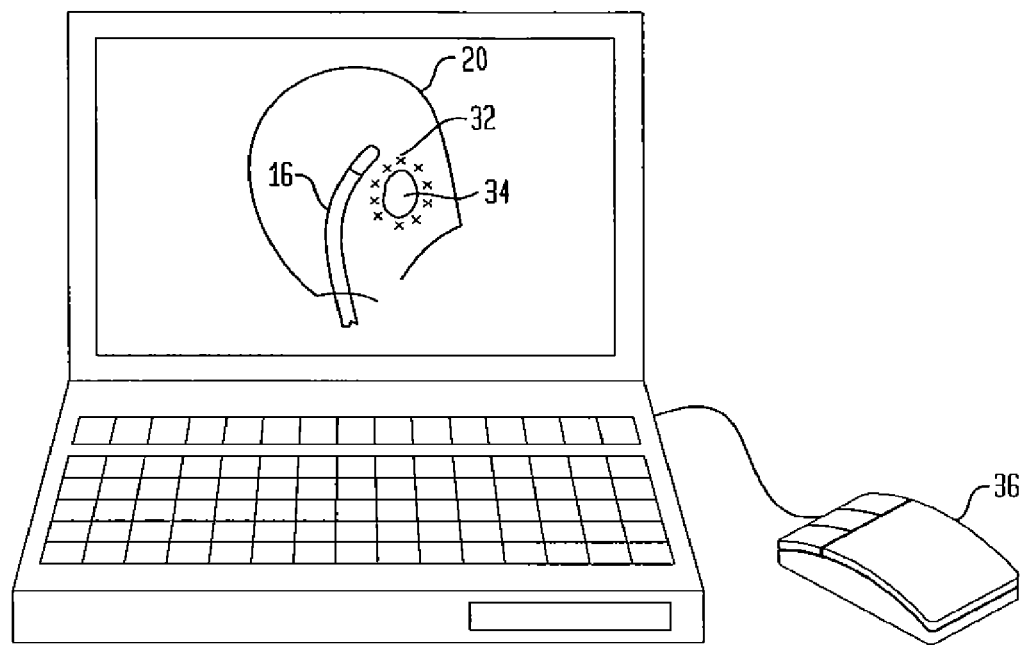
FIG. 2 is a schematic representation of a portion of the overall system.
Figure 3:
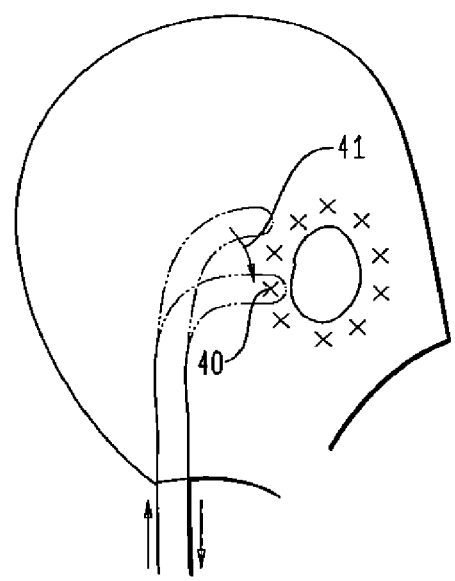
FIG. 3 is a schematic representation of an image displayed by the system.

FIG. 2 shows the interaction of the physician with the heart model. The locations for ablation are shown on the map 20 as X's 32 which surround an anatomic structure that may be, for example, the pulmonary vein 34. These locations are typically accessed on the map image through a mouse or other pointer device 36 so that the physician may act intuitively with the model. As is clear from the Ensite operation manual the catheter 16 may also be shown on the image to facilitate planning of the intervention. Turning to FIG. 3 the servo catheter 16 has been activated and the catheter has been retracted slightly as indicated by arrow 41 and has been manipulated to come into contact with the cardiac tissue at location 40. In this instance the physician is in a position to perform his ablation.

Figure 4B:
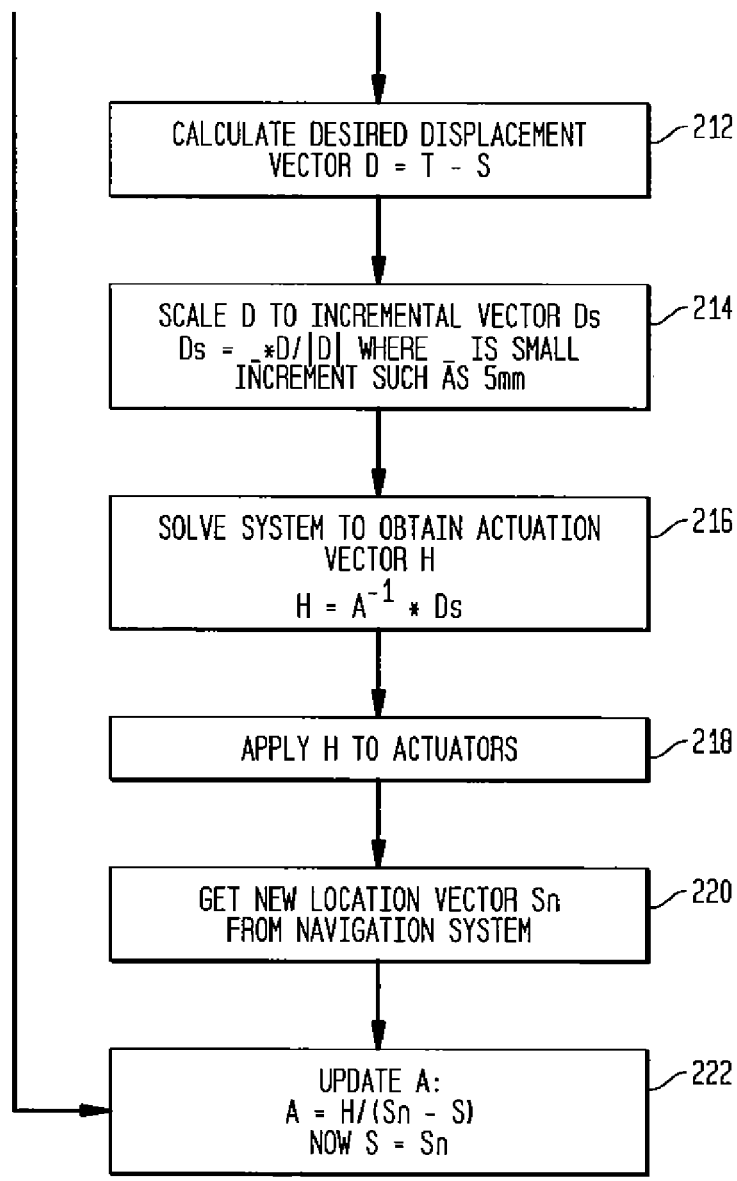
FIG. 4B is a flow chart representation of a method of the system.

The control system to achieve this result is shown in FIG. 4A and FIG. 4B which are two panels of a software flow chart describing software executed by the Ensite work station.

Turning to FIG. 4a, initially the catheter is placed in the desired heart chamber as seen in FIG. 2 by the positioning of catheter 16 as represented on the Ensite work station within the chamber of the heart 20. This process occurs after the creation of the chamber geometry. In block 202 the Ensite system determines the location of the location ring of catheter 16 in the chamber and in process 204 a small motion is initiated by the operation of the steppers 32 controlling the various pull wires of the catheter. The Ensite system tracks the motion of the location electrode and establishes a relationship between the operation of the various pull wires and motion in the chamber. It is important to note that this process eliminates the need to keep track of the X, Y, Z references of the body and the catheter. In process 206 the physician manipulates the joystick or other control mechanism and places the target location, for example target location 32, around an anatomic feature of interest, for example the OS of the pulmonary vein. The user then activates a "go" command on the workstation and the catheter 16 automatically navigates to the location 32 by measuring the difference between its current position and the desired location position in block 210. If it is within 0.5 millimeters or so, the process stops in block 212. However, if the catheter is farther away from the target location than 0.5 millimeters, the process defaults to step 212 wherein a displacement vector is calculated in process 212. In process 214 the displacement vector is scaled and in process 216 an actuation vector is computed to drive the catheter toward the location. In process 218 the actuation vector is applied to the pull wires 32 and to the carriage 28 to move the catheter tip toward the desired location. After a short incremental motion in process 220 a new location for the catheter is computed and the process repeats with comparison step 210. It is expected that in most instances the algorithm will converge and the catheter will move smoothly and quickly to the desired location. However, after a certain number of tries if this result is not achieved it is expected that an error condition will be noted and the physician will reposition the catheter manually and then restart the automatic algorithm.

What is claimed is:

1. A robotic catheter system, comprising:
   a navigation system;
   a translation servo mechanism;
   at least one deflection servo mechanism, each of the at least one deflection servo mechanisms including connection points for at least one pull wire; and
   an interactive control system running control software that:
      receives as input a target site;
      receives as input, from the navigation system, an instantaneous catheter position; and
      actuates the translation servo mechanism and the at least one deflection servo mechanism to automatically move a catheter to the target site.

2. The robotic catheter system according to claim 1, wherein at least one of the translation servo mechanism and the at least one deflection servo mechanism comprises a stepper mechanism.

3. The robotic catheter system according to claim 1, wherein at least one of the translation servo mechanism and the at least one deflection servo mechanism comprises a ball screw slider mechanism.

4. The robotic catheter system according to claim 1, wherein the control software further:
   receives an input from at least one force transducer; and
   actuates the translation servo mechanism and the at least one deflection servo mechanism based upon the input received from the at least one force transducer.

5. The robotic catheter system according to claim 1, wherein the control software actuates the translation servo mechanism and the at least one deflection servo mechanism by iteratively:
   comparing the instantaneous catheter position to the target site; and
   displacing the catheter an incremental amount towards the target site; and
   until a difference between the instantaneous catheter position and the target site is below a tolerance threshold.

6. The robotic catheter system according to claim 5, wherein the tolerance threshold is about 0.5 millimeters.

7. The robotic catheter system according to claim 1, further comprising a catheter having a deflection mechanism comprising one or more pull wires coupled to one or more pull rings.

8. The robotic catheter system according to claim 1, wherein the interactive control system further comprises:
   a display for displaying a model of a patient's anatomy; and
   a input device for selecting the target site on the displayed model of the patient's anatomy.

9. The robotic catheter system according to claim 1, wherein the control software further:
   computes an actuation vector for the translation servo mechanism and each of the at least one deflection servo mechanisms, wherein each actuation vector relates servo mechanism inputs to catheter movement outputs; and
   stores the computed actuation vectors in an actuation matrix.

10. A catheter system comprising:
    a catheter having a distal end and a deflection mechanism operable to deflect the distal end of the catheter;
    at least one electrode positioned near the distal end of the catheter;
    a first servo mechanism operably coupled to the deflection mechanism for deflecting the distal end of the catheter;
    a mapping system for detecting a position of the catheter in space; and
    control software that:
       receives as input a target site for the catheter;
       receives as input the position of the catheter in space; and
       actuates the first servo mechanism to automatically move the catheter from the position of the catheter in space to the target site for the catheter.

11. The system according to claim 10, further comprising a second servo mechanism operably coupled to the catheter for advancing and retracting the catheter, and wherein the control software actuates the first and second servo mechanisms to automatically move the catheter from the position of the catheter in space to the target site for the catheter.

12. The system according to claim 11, wherein the second servo mechanism comprises a ball screw mechanism.

13. The system according to claim 10, wherein the catheter further comprises a force transducer.

14. The system according to claim 10, wherein the first servo mechanism comprises a stepper mechanism.

15. The system according to claim 10, wherein the first servo mechanism comprises a ball screw mechanism.

16. A method of navigating a catheter within a patient, comprising:
    connecting a catheter having at least one deflection mechanism to one or more servo mechanisms;
    connecting an interactive control system to the one or more servo mechanisms;
    connecting a mapping system to the interactive control system;
    receiving, via the interactive control system, a target site for the catheter within the patient;
    measuring, via the mapping system, a location of the catheter within the patient; and
    automatically actuating the one or more servo mechanisms to navigate the catheter from the location of the catheter within the patient to the target site for the catheter within the patient.

17. The method according to claim 16, wherein the at least one deflection mechanism comprises at least one pull wire, and wherein the step of automatically actuating the one or more servo mechanisms comprises automatically actuating the one or more servo mechanisms to place the at least one pull wire in tension, thereby deflecting a distal end of the catheter.

18. The method according to claim 16, further comprising computing an actuation matrix that relates servo mechanism movements to catheter movements.

19. The method according to claim 16, wherein the step of automatically actuating the one or more servo mechanisms to navigate the catheter from the location of the catheter within the patient to the target site for the catheter within the patient comprises navigating the catheter from the location of the catheter within the patient to a point within about 0.5 mm of the target site.

20. The method according to claim 16, further comprising displaying a model of a portion of the patient's anatomy, and wherein the step of receiving, via the interactive control system, a target site for the catheter within the patient comprises using the interactive control system to identify the target site on the displayed model.

* * * * *